United States Patent [19]

Clark

[11] 4,366,076

[45] Dec. 28, 1982

[54] CORROSION INHIBITED COMPOSITIONS

[75] Inventor: David R. Clark, Sale, England

[73] Assignee: Ciba-Geigy Corporation, Ardsley, N.Y.

[21] Appl. No.: 267,309

[22] Filed: May 28, 1981

[30] Foreign Application Priority Data

Jun. 11, 1980 [GB] United Kingdom ............... 8019126

[51] Int. Cl.$^3$ .................. C10M 1/20; C10M 1/32; C10M 3/04
[52] U.S. Cl. ........................... 252/34; 252/39; 252/41; 252/49.3; 252/49.5; 252/51.5 A; 252/56 R; 252/76; 252/79; 252/392; 252/396; 260/501.17; 562/508; 562/577; 562/578; 544/107
[58] Field of Search ............... 252/34, 39, 41, 49.3, 252/49.5, 51.5 A, 56 R, 76, 79, 392, 396; 260/501.17; 544/107; 562/508, 577, 578

[56] References Cited

U.S. PATENT DOCUMENTS

| | | | |
|---|---|---|---|
| 2,688,595 | 9/1954 | Fainman ................ | 260/501.17 X |
| 2,820,805 | 1/1958 | Beets et al. ............ | 260/413 |
| 3,012,071 | 12/1961 | Gilby ................... | 260/514 |
| 3,763,231 | 10/1973 | Bruson et al. ......... | 260/537 R |
| 3,965,027 | 6/1976 | Boffardi et al. ....... | 260/501.17 X |
| 3,989,637 | 11/1976 | Hogue et al. .......... | 252/180 |
| 4,078,144 | 3/1978 | Lavigne ................ | 560/126 |
| 4,102,701 | 7/1978 | Campbell et al. ..... | 106/111 |
| 4,124,608 | 11/1978 | Larkin .................. | 260/405 |
| 4,273,664 | 6/1981 | Brandolese ............ | 252/49.5 |

FOREIGN PATENT DOCUMENTS 656378 11/1964 Belgium ........................... 252/56 R
52-38430 3/1977 Japan .
72 3537 9/1973 Netherlands .
578945 7/1946 United Kingdom .

OTHER PUBLICATIONS

CA, 52, 10160h, (1958).
CA, 41, 2237a, (1947).
CA, 87, 43168z, (1977).

Primary Examiner—W. J. Shine
Attorney, Agent, or Firm—Luther A. R. Hall

[57] ABSTRACT

Corrosion-inhibited compositions are described comprising a functional fluid in contact with a ferrous metal and, as corrosion inhibitor, a compound having the formula:

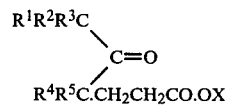

wherein X is H, an alkali- or alkaline earth metal, $NH_4$, the residue of a protonated amine, or the group —OX is the residue of an alkanol having from 1 to 20 carbon atoms or of di-, tri- or tetra-ol having from 2 to 12 carbon atoms; $R^1$, $R^2$ and $R^4$ are the same or different and each is H or —$CH_2CH_2COOX$ wherein X has its previous meaning; $R^3$ and $R^5$ are the same or different and each is H, —$CH_2CH_2COOX$ wherein X has its previous meaning, or $R^3$ or $R^5$ is a straight- or branched chain alkyl group having from 3 to 16 carbon atoms; or $R^3$ and $R^5$, together with the carbon atom to which they are each attached, may form a cycloalkanone ring containing from 5 to 15 carbon atoms.

22 Claims, No Drawings

CORROSION INHIBITED COMPOSITIONS

The present invention relates to compositions comprising a functional fluid in contact with a ferrous metal and, as corrosion inhibitor, 5-ketocarboxylic acid derivatives.

The present invention provides a composition comprising a functional fluid in contact with a ferrous metal and, as corrosion inhibitor, a compound having the formula:

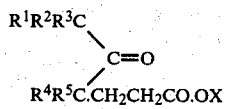

wherein X is H, alkali- or alkaline earth metal, preferably Na, K, NH$_4$, the residue of a protonated amine, or the group —OX is the residue of an alkanol having from 1 to 20 carbon atoms; or of a di-, tri- or tetra-ol having from 2 to 12 carbon atoms; R$^1$, R$^2$ and R$^4$ are the same or different and each is H or —CH$_2$CH$_2$COOX wherein X has its previous meaning; R$^3$ and R$^5$ are the same or different and each is H, —CH$_2$CH$_2$COOX wherein X has its previous meaning, or R$^3$ or R$^5$ is a straight or branched chain alkyl group having from 3 to 16, preferably 7 to 12 carbon atoms; or R$^3$ and R$^5$, together with the carbon atom to which they are attached, may form a cycloalkanone ring containing from 5 to 15 carbon atoms.

When X is the residue of a protonated amine it may be the residue of an alkylamine containing from 1 to 20 carbon atoms e.g. methylamine, ethylamine, propylamine, butylamine, hexylamine, octylamine, laurylamine, stearylamine or eicosylamine; di- or triethanolamine; or a heterocycle containing nitrogen e.g. morpholine.

Groups —OX which are the residues of 1–20 C alkanols include methoxy, ethoxy, propoxy, butoxy, hexyloxy, octyloxy, nonyloxy, decyloxy, dodecyloxy, stearyloxy and eicosyloxy groups. Groups —OX which are the residues of a 2–12 C di-, tri- or tetra-ol include the residues of ethylene glycol, propylene glycol, diethylene glycol, butylene glycol, neopentyl glycol, trimethylol propane and pentaerythritol.

Alkyl groups R$^3$ and R$^5$ include n-, sec- and tert. isomers of propyl, butyl, amyl, hexyl, heptyl, octyl, nonyl, decyl, dodecyl, tetradecyl and hexadecyl groups.

A preferred class of compounds of formula I is that having the formula:

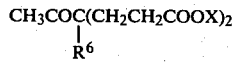

wherein X has its previous significance and R$^6$ is a straight- or branched alkyl group having from 6 to 16, preferably from 7 to 12 carbon atoms.

A further preferred class is that of the formula:

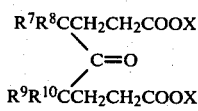

wherein X has its previous significance, R$^7$ and R$^{10}$ are the same or different and each is a straight- or branched alkyl group having from 3 to 10 carbon atoms and R$^8$ and R$^9$ are the same or different and each is H or —CH$_2$CH$_2$COOX wherein X has its previous significance.

A still further preferred class is that having the formula:

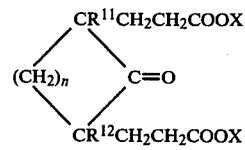

wherein X has its previous significance, R$^{11}$ and R$^{12}$ are the same or different and each is H or —CH$_2$CH$_2$COOX wherein X has its previous significance, and n is an integer from 5 to 15, preferably 9 to 11.

Specific examples of compounds of formula I are:
4-n-heptyl-4-acetyl pimelic acid,
4-n-octyl-4-acetyl pimelic acid,
4-n-nonyl-4-acetyl pimelic acid,
4-n-decyl-4-acetyl pimelic acid,
4-n-dodecyl-4-acetyl pimelic acid,
4-n-tetradecyl-4-acetyl pimelic acid,
2,2,10-tris(2'-carboxyethyl)cyclodecanone,
2,2,12-tris(2'-carboxyethyl)cyclododecanone,
2,2,13-tris(2'-carboxyethyl)-cyclotridecanone,
5,7,7-tris(2'-carboxyethyl)-undecan-6-one,
6,8,8-tris(2'-carboxyethyl)-tridecan-7-one and
8,10,10-tris(2'-carboxyethyl)-heptadecan-9-one
as well as their salts, e.g. Na, K and NH$_4$ salts, protonated amine analogues and ester analogues, e.g. their mono- and di-ester analogues.

The compounds of formula I are known compounds having been described, with a method of production, e.g. in British Patent Specification No. 1490287. However, the utility ascribed therein to the compounds of formula I was restricted to their function in controlling the setting of plaster.

Preferably, the composition of the present invention contains from 0.001% to 5% by weight of the compound of formula I, based on the total weight of the composition.

Examples of functional fluids which are useful in the compositions of the present invention include purely aqueous systems e.g. cooling water systems; non-aqueous systems such as lubricants having a mineral oil or synthetic carboxylic acid ester base, greases, temporary protectants and hydraulic fluids based on mineral oils or phosphate esters; and mixed aqueous/non-aqueous systems e.g. aqueous polyglycol/polyglycol ether mixtures, glycol systems, oil-in-water and water-in-oil emulsions, metal-working fluids having, as their base, mineral oils or aqueous systems, and aqueous-based paints.

For the treatment of aqueous-based systems e.g. cooling water systems those compounds are preferred which (a) have the formula

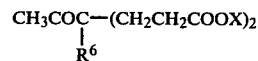

or their mono-carboxyethyl analogues wherein X has its previous significance and is preferably H, Na or K; and R$^6$ has its previous significance and is preferably an alkyl group containing from 3 to 16, preferably 7 to 12, carbon atoms, especially an octyl group; or (b) have the formula:

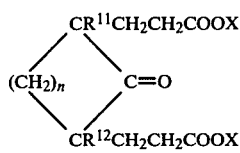

wherein X has its previous significance and is preferably H, Na or K; $R^{11}$ is H or $—CH_2CH_2COOX$ wherein X has its previous significance and $R^{11}$ is preferably H; $R^{12}$ is H or $—CH_2CH_2COOX$ wherein X has its previous significance and $R^{12}$ is preferably $—CH_2CH_2COOX$ (wherein X has its previous significance); and n is an integer from 5 to 15, preferably 9 to 11.

For the treatment of metal working fluids, those compounds are preferred which:

(a) have the formula $CH_3COC(R^6)(CH_2CH_2COOX)_2$ and their mono (carboxyethyl) analogues wherein X has its previous significance and is preferably H, diethanolamine, morpholine or, especially, triethanolamine; and $R^6$ has its previous significance and is preferably an octyl or decyl group;

(b) have the formula:

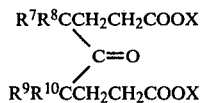

wherein X has its previous significance and is preferably H, diethanolamine or morpholine or especially, triethanolamine; $R^8$ and $R^9$ are the same or different and each is H or $CH_2CH_2COOX$ wherein X has its previous significance and $R^8$ is especially H; and $R^7$ and $R^{10}$ are the same or different and each is an alkyl group having 3–10 C atoms and each is preferably an amyl group;

(c) have the formula:

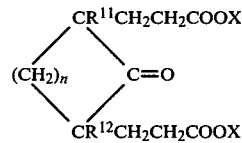

wherein X has its previous significance and is preferably H, diethanolamine, morpholine or, especially, triethanolamine; $R^{11}$ has its previous significance and is, especially, H; $R^{12}$ has its previous significance and is preferably $CH_2CH_2COOX$, and n has its previous significance and is preferably 9 to 11.

For the treatment of oil-based functional fluids, those compounds are preferred which have the formula I as hereinbefore defined wherein (a) $R^1$, $R^2$ and $R^3$ are each H; $R^4$ has its previous significance; $R^5$ is an alkyl group having from 8 to 16 carbon atoms; and X is preferably H or a protonated amine, or X is an alkyl or hydroxyalkyl function when $R^4$ is $—CH_2CH_2COOH$;

(b) $R^1$ is H, $R^2$ and $R^4$ are either each H or one is H and the other is $—CH_2CH_2COOX$; $R^3$ and $R^5$ are alkyl having from 5 to 16 carbon atoms, especially from 8 to 16 carbon atoms; and X is H or a protonated amine or X is an ester function (alkyl or hydroxyalkyl) when $R^2$ or $R^4$ is $—CH_2CH_2COOH$; or (c) $R^1$ is H; $R^2$ and $R^4$ are either each H or one is H and the other is $—CH_2CH_2COOX$; $R^3$ and $R^5$ are the group $—(CH_2)_m—$, wherein m is an integer from 9 to 15; and X is H or a protonated amine or X is an ester function when $R^2$ or $R^4$ is $CH_2CH_2COOH$.

In compositions of the invention comprising purely aqueous functional fluids e.g. cooling water systems of the present invention, compounds of formula I may be used singly or in admixture with other additives e.g. known corrosion inhibitors such as phosphonates, phosphonocarboxylic acids as well as N-acyl sarcosines, imidazolidines, triethanolamine and fatty amines and polycarboxylic acids; water-soluble azoles e.g. triazoles such as benzotriazole and other copperpassivating derivatives, e.g. 2-mercapto-benzothiazole. Further preferred co-additives are dispersing and/or threshold agents, such as for example polymerised acrylic acid and its salts, hydrolysed polyacrylonitrile, polymerised methacrylic acid and its salts, polyacrylamide and copolymers thereof from acrylic and methacrylic acids, lignin sulphonic acid and its salts, tannin, naphthalene sulphonic acid/formaldehyde condensation products, starch and its derivatives, and cellulose. Specific threshold agents such as, for example, alkyl phosphonic acids, 1-aminoalkyl-1,1-diphosphonic acids and their salts, polycarboxylic acids e.g. polymaleic acids and alkali metal phosphates, may also be used together with the compounds of formula I.

Precipitating agents such as alkali metal orthophosphates, carbonates; oxygen scavengers such as alkali metal sulphites and hydrazines; sequestering agents such as nitrilotriacetic acid and their salts, ethylene diamine tetraacetic acid and its salts; antifoaming agents such as distearylsebacamide, distearyl adipamide and related products derived from ethylene oxide and/or propylene oxide condensations, in addition to fatty alcohols, such as capryl alcohols and their ethylene oxide condensates; may also be used together with the compound of formula I.

Examples of co-additives suitable in non-aqueous functional fluids are antioxidants, metal passivators, rust inhibitors, viscosity index improvers, pour-point depressants, dispersants, detergents, extreme pressure and anti-wear additives.

Examples of antioxidants are:

(a) Alkylated and non-alkylated aromatic amines and mixtures thereof e.g. dioctyldiphenylamine; mono-t-octylphenyl-α and β-naphthylamines; dioctylphenothiazine; phenyl-α-naphthylamine: N,N'-di-sec. butyl p-phenylenediamine.

(b) Hindered phenols e.g. 2,6-ditertiarybutyl-p-cresol; 4,4'-bis-(2,6-diisopropylphenol); 2,4,6-triisopropyl phenol; 2,2'-thio-bis-(4-methyl-6-tertbutylphenol).

(c) Alkyl, aryl or alkaryl phosphites e.g. triphenylphosphite; trinonylphosphite; diphenyldecylphosphite.

(d) Esters of thiodipropionic acid e.g. dilaurylthiodipropionate.

(e) Salts of carbamic and dithiophosphoric acids e.g. antimony diamyldithiocarbamate, zinc diamyldithiophosphate.

(f) Metal salts, complexes of organic chelative agents e.g. copper bis (trifluoroacetonates), copper phthalocyanine, tributyl ester of EDTA, mono sodium salt.

(g) Free radical antioxidants and their precursors e.g. nitroxides.

(h) Combinations of two or more antioxidants from any of the above sections i.e. an alkylated amine and a hindered phenol.

Examples of Metal Passivators are:

(a) for copper e.g. benzotriazole, 5,5'-methylene-bis-benzotriazole, 4,5,6,7-tetrahydrobenzotriazole, 2,5-dimercaptothiadiazole, salicylidenepropylenediamine, salts of salicylaminoguanidine; quinizarin.

(b) for magnesium e.g. pyridylamines.

(c) for lead e.g. sebacid acid, propylgallate and quinizarin.

(d) combinations of two or more of the above additives.

Examples of Rust Inhibitors are:

(a) Organic acids, and their esters, metal salts, anhydrides e.g. N-oleoyl sarcosine, sorbitan mono-oleate, lead naphthenate, dodecenylsuccinic anhydride.

(b) Nitrogen containing materials e.g.

(i) Primary, secondary or tertiary aliphatic or cycloaliphatic amines and amine salts of organic and inorganic acids e.g. morpholine, stearyl amine, triethanolamine caprylate.

(ii) heterocyclic compounds e.g. imidazolines, oxazolines.

(c) Phosphorus containing materials e.g. inorganic phosphates, phosphonic acids, amine phosphates (d) Sulphur containing materials e.g. barium dinonylnaphthalene sulphonates.

(e) Combinations of two or more of the above additives. Examples of Viscosity Index Improvers/Pour Point Depressants are:

e.g. polyacrylates, polybutenes, polyvinyl pyrrolidones.

Examples of Dispersant/Detergents are:

e.g. metal sulphonates (Ca, Ba, Mg) and phenates, polybutenyl succinimides.

Examples of Extreme Pressure/Antiwear Additives are: sulphur and/or phosphorus and/or halogen containing materials e.g. sulphurised sperm oil, tritolylphosphate, chlorinated paraffins. For compositions of the invention in which the functional fluid is a mixed aqueous/non-aqueous system, the compounds of formula I may be used alone or in admixture with other compounds e.g. with known corrosion inhibitors and, in the case of machining fluids, with an extreme-pressure additive.

Examples of other corrosion inhibitors which may be present in the aqueous systems of the present invention in addition to the amine salts of the compounds of formula I include the following groups:

(a) Organic acids, their esters or ammonium, amine, alkanolamine and metal salts, for example, benzoic acid, p-tert.butyl benzoic acid, disodium sebacate, triethanolamine laurate, iso-nonanoic acid, triethanolamine salt of (p-toluene sulphonamido caproic acid), sodium N lauroyl sarcosinate or nonyl phenoxy acetic acid;

(b) Nitrogen containing materials such as the following types: fatty acid alkanolamides; imidazolines, for example 1-hydroxy-ethyl-2-oleylimidazoline; oxazolines; triazoles for example benzotriazoles; and inorganic salts, for example sodium nitrite and nitrate;

(c) Phosphorus containing materials such as the following types: amine phosphates, phosphonic acids or inorganic salts, for example sodium dihydrogen phosphate;

(d) Sulphur containing compounds such as the following types: sodium, calcium or barium petroleum sulphonates, or heterocyclics for example sodium mercaptobenzothiazole.

Examples of extreme pressure additives which may be present in the fluids of the present invention include sulphur and/or phosphorus and/or halogen containing materials for instance sulphurised sperm oil, sulphurised fats, tritolyl phosphate, chlorinated paraffins or ethoxylated phosphate esters.

The following Examples further illustrate the present invention. Parts and percentages by weight unless otherwise stated. Starting materials (products of Examples 1 to 1X) and their production are described generically in British Patent Specification No. 1490287.

PRODUCTION OF STARTING MATERIALS

Example I 3 parts potassium hydroxide dissolved in 7 parts methanol were added to a solution of 170 parts 2-undecanone in 200 parts t-butanol. The mixture was cooled to 5° C. whereupon a solution of 106 parts acrylonitrile in 120 parts t-butanol was added over a period of three hours maintaining the temperatures of 5° to 10° C. When the addition was complete, the reaction was allowed to warm to room temperature and stirred for four hours. After addition of 5 parts concentrated hydrochloric acid (diluted with water to 15 parts) to neutralise the catalyst, the solvents and unreacted acrylonitrile were removed by distillation.

The residue was partitioned between ether and water, and the ethereal phase collected, dried over magnesium sulphate, the ether removed, and the residue distilled under vacuum.

After removal of 5 parts of unreacted ketone (boiling range 60°–65° C./0.6 mm Hg) a fraction (A) distilling at 125°–135° C./0.5 mm Hg was collected (38 parts: representing a yield of 17% based on ketone) and identified as 4-acetyl dodeca nitrile by n.m.r. and elemental analysis:

$C_{14}H_{25}NO$ requires: C 75.28%; H 11.28%; N 6.27%. Found: C 75.56%; H 11.18% N 6.54%.

A second fraction (B), distilling at 209°–212° C./0.3 mm Hg was collected (215 parts: representing a yield of 78% based on ketone) and identified as 4-n-octyl-4-acetyl-pimelonitrile by n.m.r. and elemental analysis:

$C_{17}H_{28}N_2O$ requires: C 73.91%; H 10.14%; N 10.14%. Found: C 73.41%; H 10.41%; N 10.52%.

138 parts of fraction B were added to a solution of 99 parts of potassium hydroxide pellets (assay 85%) in 600 parts water and the mixture heated to reflux with stirring. After refluxing for eight hours the solution was cooled, neutralised with concentrated hydrochloric acid to pH 2, and the precipitated syrupy solid extracted with ether. After washing and drying the ether solution, the solvent was removed leaving a solid residue which was recrystallised from ethyl acetate/petroleum spirit giving 131 parts (90% yield) of 4-n-octyl-4-acetyl pimelic acid (melting point 69°–71° C.) identified by n.m.r. and elemental analysis:

$C_{17}H_{30}O_5$ requires: C 64.94%; H 9.62%. Found: C 65.15%; H 9.71%.

Example II 22.3 parts of fraction A (described in Example I) were added to a solution of 13.2 parts 85% potassium hydroxide in 100 parts water. The mixture was heated to reflux and maintained for six hours whereupon the solution was cooled and neutralised with concentrated hydrochloric acid to pH 2.

The precipitated oil was extracted with ether, the ether solution washed with water, dried over magnesium sulphate and the solvent removed. The residue solidified on standing and was recrystallised from 40°-60° petroleum spirit giving 21.3 parts (88% yield) of 4-acetyldodecanoic acid (melting point 36°-38° C.) identified by n.m.r. and elemental analysis:

$C_{14}H_{26}O_3$ requires: C 69.38%; H 10.81%. Found: C 69.02%; H 10.58%.

When incorporated into an aqueous functional fluid in contact with a ferrous metal, 4-acetyldodecanoic acid exhibited excellent corrosion inhibitor activity.

Example III

In a manner analagous to that described in Example I, 99 parts of 2-tridecanone were treated with 53 parts of acrylonitrile in t-butanol. After work-up, distillation afforded a fraction (A) distilling at 159°-165° C./0.2 mm Hg (33 parts: representing a yield of 26% based on ketone) identified as 4-acetylmyristonitrile by n.m.r. and elemental analysis:

$C_{16}H_{29}NO$ requires: C 76.49%; H 11.55%; N 5.58%. Found: C 77.00%; H 11.53%; N 5.58%.

The residue was not further distilled but was identified by n.m.r., glc, and elemental analysis as being substantially (>95%) 4-n-decyl-4-acetylpimelonitrile (107 parts, 70% yield)

$C_{19}H_{32}N_2O$ requires: C 75.00%; H 10.53%; N 9.21%. Found: C 74.52%; H 10.19%; N 9.41%.

The residue was hydrolysed as described in Example I to yield 107 parts (75% yield) of 4-n-decyl-4-acetylpimelic acid, crystallised from ethyl acetate/petroleum spirit.

$C_{19}H_{34}O_5$ requires: C 66.63%; H 10.01%; N 23.36%. Found: C 66.62%; H 9.81%; N 23.57%.

Example IV 25 parts of fraction A described in Example III were hydrolysed in a manner previously described to yield 23 parts (84% yield) of 4-acetylmyristic acid:

$C_{16}H_{30}O_3$ requires: C 71.11%; H 11.11%. Found: C 71.23%; H 11.55%.

When incorporated into an aqueous functional fluid, 4-acetylmyristic acid exhibited excellent corrosion inhibitor activity.

Example V 1.7 parts potassium hydroxide dissolved in 4 parts methanol were added to a slurry of 100 parts cyclododecanone in 100 parts t-butanol. The mixture was cooled to 10° C. and a solution of 117 parts acrylonitrile in 60 parts t-butanol was added dropwise over 1¼ hours maintaining the temperature below 20° C. When the addition was complete, upon being allowed to warm to room temperature, precipitation of the cyanoethyl intermediate spontaneously occurred. This was filtered, washed with ether and identified, by the techniques of Example I as being substantially (>90%) 2,2,12-tris(2'-cyanoethyl)cyclododecanone (175 parts; 93%; m.pt 93°-98° C.):

$C_{21}H_{31}N_3O$ requires: C 73.86%; H 9.15%; N 12.31%. Found: C 72.91%; H 8.81%; N 12.71%.

The cyanoethyl intermediate was then added to a solution of 135 parts potassium hydroxide (85% assay) in 550 parts water and the mixture refluxed 17 hours. After cooling, concentrated hydrochloric acid (approximately 200 parts) was added to pH 2 to precipitate the product, 2,2,12-tris(2'-carboxyethyl)-cyclododecanone. This was filtered, washed thoroughly with warm water, and dried to yield 176 parts (86.5% yield), m.pt 187°-190° C.:

$C_{21}H_{34}O_7$ requires: C 63.29%; H 8.60%. Found: C 63.09%; H 8.27%.

Further examples, utilising symmetrical dialkyl ketones and adopting the procedures outlined in previous Examples, are listed in Table I. Each of Examples VI to VIII utilises a ketone: acrylonitrile molar ratio of 1:3 for the cyanoethylation stage.

TABLE I

Tris carboxyethyl alkanones $$CH_3(CH_2)_n C(CH_2CH_2COOH)_2\!-\!C(=O)\!-\!CHCH_2CH_2COOH\,CH_3(CH_2)_n$$

| Example | Ketone starting material | n | Nature of product | Yield (% based on ketone) | Elemental analyses | C | H |
|---|---|---|---|---|---|---|---|
| VI | 6-undecanone | 3 | Viscous brown syrup | 91 | $C_{20}H_{34}O_7$ requires: found: | 62.15% 61.75% | 8.87% 8.98% |
| VII | 7-tridecanone | 4 | Viscous brown syrup | 89 | $C_{22}H_{38}O_7$ requires: found: | 63.74% 63.19% | 9.23% 9.14% |
| VII | 9-heptadecanone | 6 | Viscous brown syrup | 74 | $C_{26}H_{46}O_7$ requires: found: | 66.35% 65.67% | 9.85% 9.48% |

Example IX 14.2 parts of 4-n-octyl-4-acetylpimelic acid and 3.5 parts of 1,2-propylene glycol were refluxed in 50 parts toluene until 0.9 parts water were removed by azeotropic distillation. The reaction mixture was cooled and the toluene removed under reduced pressure to yield 16 parts of a waxy solid having an acid value of 247 mg KOH/g.

Examples 1 to 3

Corrosion inhibitor activity of the products of Examples I, II and V was demonstrated in the following way, by the Aerated Solution Bottle Test, using as test water an artificial soft water, having the following characteristics:

| | |
|---|---|
| pH | 7.0 |
| Phenol alkalinity | 0 |
| Total alkalinity | 20 ppm as $CaCO_3$ |
| Total hardness | 35 ppm as $CaCO_3$ |
| Chloride ion | 10 ppm as NaCl |
| Ryznev Index | 10.4 |

Mild steel coupons, measuring 5 cms×1.5 cms, are scrubbed with pumice, immersed for one minute in hydrochloric acid and then rinsed, dried and weighed.

The desired proportion (50 or 100 ppm) of the corrosion inhibitor under test was then dissolved in the test water. A steel coupon is suspended in the solution, and the whole is stored in a bottle in a thermostat at 40° C. During the storage period, air is passed into the solution at 500 ml/minute, the passage of the air being screened from the steel coupon; any water losses by evaporation are replaced as they occur with distilled water from a constant head apparatus.

After 48 hours, the steel coupon is removed, scrubbed with pumice, immersed for one minute in hydrochloric acid inhibited with 1% by weight of hexamine and then rinsed, dried and reweighed. A certain loss in weight was observed to have occurred. A blank test i.e. immersion of a mild steel specimen in the test water in the absence of any potential corrosion inhibitor, is carried out with each series of tests. The corrosion rates are calculated in milligrams of weight loss/sq. decimeter/day (m.d.d.) but for convenience the results are shown as percentage protection, which is defined as follows:

$$\% \text{ Protection} = \frac{[\text{Blank corrosion rate (in mdd)} - \text{Sample corrosion rate (in mdd)}] \times 100}{\text{Corrosion rate for blank (in mdd)}}$$

The results obtained are set out in the following Table II

TABLE II

% Protection in artificial soft water

| Example | Test Compound | Artificial soft water 100 ppm |
|---|---|---|
| — | 4-acetyl-4-n-amyl pimelic acid | 80 |
| — | 4-acetyl-4-methyl pimelic acid | 68 |
| — | 1,1,1-tris(2'-carboxyethyl) acetone | +63 |
| — | 2,2,6,6-tetra(2'-carboxyethyl) cyclohexanone | 54 |
| — | 4-methyl-2,2,6,6-tetra-(2'-carboxyethyl) cyclohexanone | 31 |
| — | 4-t-butyl-2,2,6,6-tetra-(2'-carboxyethyl)cylcohexanone | 30 |
| — | 1,1,1-tris-(2'-carboxyethyl) acetophenone | 27 |
| 1 | 4-n-octyl-4-acetylpimelic acid | 99 |
| 2 | 4-actyldodecanoic acid | 99 |
| 3 | 2,2,12-tris-(2'-carboxyethyl)-cyclododecanone | 96 |

N.B. + sign is indicative of aggressive corrosion (viz. a corrosive affect over and above that experienced in the absence of any test compound).

The results in Table II demonstrate the outstanding corrosion inhibition exhibited by the compositions of the invention relative to a composition containing compounds of chemical structures very close to those used in Examples 1 to 3.

Examples 4 and 5

Evaluation of Corrosion Inhibition by a Laboratory Heat Exchanger Rig Test

In this rig, corrosive water is aerated and circulated over a number of metal coupons, and is heated by being passed through a heated steel heat exchanger tube. After a suitable test period, the metal coupons and the heat exchanger tube are examined, and their state assessed.

In detail, the rig consists of a closed water circuit, made up of the following items in order,
20 liter reservoir
1 liter reservoir
flow meter
coupon chamber
heat exchanger
cooling condenser Corrosive water in the 20 liter reservoir is aerated with compressed air introduced through a sintered disc at about 5 liters per minute, and is then pumped to the 1 liter reservoir. From this reservoir it is pumped through the flow meter to the glass coupon chamber in which are a number of rectangular metal coupons each 2.5 by 0.0 cms. mounted on a perspex jig. The water then flows through the heat exchanger which is made up of a 1.58 cm. internal diameter steel tube with copper end pieces around which is wound a 960 watt heater coil; from the heat exchanger the water flows through the cooling condenser back to the 20 liter reservoir.

A flow rate in the circuit of about 4.55 liters per minute provides a velocity of about 0.46 meter per second and a Reynolds number of 8500 in the heat exchanger. The heater coil gives the heat exchanger tube a skin temperature of about 60° C. and the water leaves at about 45° C., a difference across the heat transfer surface of some 15° C. The cooling condenser is so operated as to cool the water to about 40° C. before it begins a fresh circuit.

Metal coupons are scrubbed with pumice and then immersed in acid as follows:

| Metal | Acid |
|---|---|
| mild steel | Conc. HCl diluted 1:1 with water at room temperature for 1 minute |
| copper | Conc. HCl diluted 1:1 with water at room temperature for 1 minute |
| brass | Conc. HCl diluted 1:1 with water at room temperature for 1 minute |
| Aluminium | 5% phosphoric acid/2% Chromic acid, at 75° C. for 5 minutes. |

After such immersion, the coupons are rinsed with water, dried and weighed; they are then mounted on a perspex jig, care being taken to ensure that none of the coupons touch each other, and that they are insulated from the bolt holding the jig together. The heat exchanger tube is cleaned with pumice, dipped in conc. hydrochloric acid diluted 1:1 with water, and then rinsed in water and dried.

The rig is assembled, and cleaned thoroughly by circulating conc. hydrochloric acid diluted 1:1 with water, then flushing with tap water for about half-an-hour (about 136.4 liters in all) and draining. The necessary quantity of additives to produce the desired concentrations is put into one of the reservoirs and the rig is filled with 22 liters of a standardized Manchester corrosive test water.

The pump is primed and started, and the heater switched on.

The concentration of inhibitor and the water level in the rig are checked daily.

After three days, and again after ten days, the heat exchanger tube is removed, sectioned and examined. The test coupons are removed and the mild steel, brass and copper coupons are cleaned as before except that the acid is inhibited with 1% hexamine, rinsed, dried and reweighed. The aluminium specimens are scrubbed, dried and reweighed.

The results observed enable an assessment to be made of the anticorrosive action of the inhibitor under test, using the same parameter of corrosion rate (in mdd) as was used in Examples 1 to 3.

Using this test procedure, the following results were obtained:

following procedure, which is a modification of the Institute of Petroleum Test 287.

1 gram of a compound under test is dissolved in water (either dionised water or a standard hard water) and sufficient triethanolamine (TEA) is added to the solution that the solution has a pH value of approximately 9. A two milliliter portion of this solution is then contacted with metal chips placed on a filter paper under the conditions set forth in the IP 287 Test Procedure.

The visual assessment of the filter paper after exposure is in accordance with the following guidelines:

| degree of rusting | rating |
| --- | --- |
| no rusting | O |
| ≦5 small specks | T (trace) |
| ≦10% area rusted | M (moderate) |
| >10% area rusted | S (severe) |

TABLE III

Evaluation of corrosion inhibition in laboratory rig

| Example | Test Compound | Amount test compound and length of test | Corrosion rate (mdd) | | | | | |
| --- | --- | --- | --- | --- | --- | --- | --- | --- |
| | | | Mild steel | cast iron | Al | Cu | brass | Mild steel heat exchanger |
| — | none | — | 140.1 | 180.2 | 5.8 | 3.7 | 4.8 | 420.6 |
| — | 4-acetyl-nonanoic acid | 100 ppm 3 days; 25 ppm 10 days | 84.9 | 90.8 | 0.0 | 0.0 | 0.0 | 283.1 |
| 4 | 4-n-octyl-4-acetyl-pimelic acid | 100 ppm 3 days; 25 ppm 10 days | 2.1 | 11.8 | 0.6 | 0.2 | 0.3 | 36.5 |
| 5 | 2,2,12-tris-(2'-carboxyethyl)cyclododecanone | 100 ppm 3 days; 25 ppm 10 days | 7.4 | 110.6 | 2.1 | 0.3 | 0.5 | 90.8 |

Examples 6 to 13

The corrosion resistance of various aqueous cutting oil compositions of the invention were assessed by the

TABLE IV

Corrosion resistance in aqueous cutting fluids

| Example | Test compound | % TEA per 1% test compound | pH | IP 287 Test Data | | |
| --- | --- | --- | --- | --- | --- | --- |
| | | | | Dilution Ratio | Rust (deionised water) | Rust (hard water) |
| — | 4-acetyl-4-n-amyl pimelic acid | 3.0 | 8.6 | 1:50 | M | S |
| | | | | 1:100 | S | — |
| | | | | 1:200 | S | — |
| — | 4-acetyl-4-methyl pimelic acid | 5.75 | 8.9 | 1:30 | S | S |
| — | 1,1,1-tris(2'-carboxyethyl) acetone | 5.25 | 8.8 | 1:32 | S | S |
| 6 | 4-n-octyl-4-acetyl pimelic acid | 3.4 | 9.0 | 1:46 | 0 | 0 |
| | | | | 1:92 | 0 | 0 |
| | | | | 1:184 | 0 | M |
| 7 | 2,2,12-tris(2'-carboxyethyl)cyclodecanone | 6.5 | 9.0 | 1:26 | 0 | 0 |
| | | | | 1:52 | 0 | 0 |
| | | | | 1:104 | 0 | M |
| 8 | 4-acetyldodecanoic acid | 4.1 | 9.0 | 1:40 | 0 | 0 |
| | | | | 1:160 | 0 | T-M |
| | | | | 1:320 | 0 | — |
| 9 | 4-n-decyl-4-acetyl pimelic acid | 4.7 | 8.9 | 1:34 | 0 | 0 |
| | | | | 1:68 | 0 | T |
| | | | | 1:136 | 0 | M |
| | | | | 1:272 | M | S |
| 10 | 2,12-bis(2'-carboxyethyl) cyclododecanone | 5.9 | 9.0 | 1:28 | 0 | 0 |
| | | | | 1:112 | 0 | M |
| | | | | 1:224 | 0 | — |
| 11 | Product of Example 6 | 5.5 | 9.0 | 1:30 | 0 | 0 |
| | | | | 1:120 | 0 | T |
| | | | | 1:240 | M | S |
| 12 | Product of Example 7 | 5.3 | 9.0 | 1:32 | 0 | 0 |
| | | | | 1:128 | 0 | T |
| | | | | 1:256 | T | — |
| 13 | Product of Example 8 | 4.9 | 9.1 | 1:34 | 0 | 0 |
| | | | | 1:68 | 0 | M |
| | | | | 1:136 | T | — |
| control | No inhibitor | — | — | 1:20 | 0 | S |
| | | | | 1:50 | M | S |

TABLE IV-continued

| | | Corrosion resistance in aqueous cutting fluids | | | |
|---|---|---|---|---|---|
| | | % TEA per 1% test | | IP 287 Test Data | |
| Example | Test compound | compound | pH | Dilution Ratio | Rust (deionised water) | Rust (hard water) |
| | | | | 1:100 | S | S |

In relation to the test results in Table IV, since an excess of TEA is present over the stoichiometric equivalent of the test acid, the latter are present as their triethanolamine salts.

Examples 14 to 19

The corrosion resistance of various oil compositions of the present invention was assessed by the ASTM D665A procedure.

In this test method, a mild steel specimen, which has been precleaned by a prescribed method, is immersed in 300 ml. of a stirred oil, containing the inhibitor under test, and maintained at 60° C., for 30 minutes. Then 30 ml. of deionised water are added and stirring at 60° C. is continued for 24 hours.

At the end of this period, the metal specimen is examined visually against the following standard:

| degree of rusting | rating |
|---|---|
| clean and bright | C + B |
| light rusting (<5 small specks) | L (light) |
| ≦10% area rusted | M (moderate) |
| >10% area rusted | S (severe) |

TABLE V

| | Corrosion resistance in oil compositions | | |
|---|---|---|---|
| | | ASTM D 665A Test | |
| Example | Test Compound | Concentration % | Degree of rusting |
| — | 4-n-acetyl-4-n-amyl pimelic acid | 0.05 | M |
| | | 0.025 | S |
| 14 | 4-n-octyl-4-acetyl pimelic acid | 0.05 | C + B |
| | | 0.013 | M |
| 15 | 4-acetyldodecanoic acid | 0.05 | C + B |
| | | 0.013 | C + B |
| 16 | 4-n-decyl-4-acetyl pimelic acid | 0.05 | C + B |
| 17 | 4-acetylmyristic acid | 0.05 | C + B |
| 18 | Product of the half-ester of Example 1 plus propylene-1,2-glycol | 0.025 | C + B |
| | | 0.013 | C + B |
| | | 0.006 | C + B |
| 19 | 3:2 mixture of the products of Examples 16 and 17 | 0.013 | C + B |
| | | 0.006 | C + B |

What we claim is:

1. A composition comprising a functional fluid in contact with a ferrous metal and, as corrosion inhibitor, a compound having the formula:

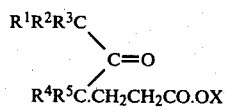

wherein X is H, an alkali- or alkaline earth metal, NH₄, the residue of a protonated amine, or the group —OX is the residue of an alkanol having from 1 to 20 carbon atoms or of a di- tri- or tetra-ol having from 2 to 12 carbon atoms; $R^1$, $R^2$ and $R^4$ are the same or different and each is H or —CH$_2$CH$_2$COOX wherein X has its previous meaning; $R^3$ and $R^5$ are the same or different and each is H, —CH$_2$CH$_2$COOX wherein X has its previous meaning, or $R^3$ or $R^5$ is a straight - or branched chain alkyl group having from 3 to 16 carbon atoms; or $R^3$ and $R^5$ together are alkylene of 5 to 15 carbon atoms.

2. A composition as claimed in claim 1 wherein X is Na, K or NH₄.

3. A composition as claimed in claim 1 or 2 wherein $R^3$ or $R^5$ is a straight- or branched chain alkyl group having from 7 to 12 carbon atoms.

4. A composition as claimed in claim 1 wherein the proportion of the compound of formula I is from 0.001% to 5% by weight, based on the total weight of the composition.

5. A composition as claimed in claim 1 wherein the base composition is an aqueous system and the inhibitor has the formula:

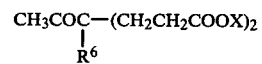

or its mono- carboxyethyl analogue, wherein X is as defined in claim 1 and $R^6$ is an alkyl group containing from 6 to 16 carbon atoms.

6. A composition as claimed in claim 5 wherein X is H, Na or K and $R^6$ is an alkyl group containing 7 to 12 carbon atoms.

7. A composition as claimed in claim 6 wherein X is H, Na or K and $R^6$ is an octyl group.

8. A composition as claimed in claim 1 wherein the base composition is an aqueous system and the inhibitor has the formula:

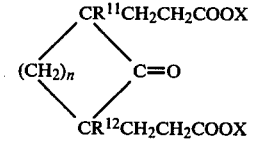

wherein X is as defined in claim 1, $R^{11}$ and $R^{12}$ are the same or different and each is H or —CH$_2$CH$_2$COOX wherein X has its previous significance and n is an integer from 5 to 15.

9. A composition as claimed in claim 8 wherein n is an integer from 9 to 11.

10. A composition as claimed in claim 8 wherein X is H, Na or K, $R^{11}$ is H, $R^{12}$ is —CH$_2$CH$_2$COOX wherein X is as defined above and n is 9.

11. A composition as claimed in claim 1 wherein the base composition is a metal working fluid and the inhibitor has the formula $$CH_3COC(CH_2CH_2COOX)_2 \quad \text{II}$$
$$\overset{|}{R^6}$$

wherein X is as defined in claim 1 and $R^6$ is an alkyl group containing from 6 to 16 carbon atoms.

12. A composition as claimed in claim 11 wherein X is H, or the protonated residue of diethanolamine, triethanolamine or morpholine, and $R^6$ is an octyl group.

13. A composition as claimed in claim 12 wherein X is the protonated residue of triethanolamine.

14. A composition as claimed in claim 1 wherein the base composition is a metal working fluid and the inhibitor has the formula:

$$R^7R^8CCH_2CH_2COOX \quad \text{III}$$
$$\diagdown$$
$$C=O$$
$$\diagup$$
$$R^9R^{10}CCH_2CH_2COOX$$

wherein X is as defined in claim 1, $R^8$ and $R^9$ are the same or different and each is H or $-CH_2CH_2COOX$ in which X is as defined in claim 1 and $R^7$ and $R^{10}$ are the same or different and each is an alkyl group having 3 to 10 C atoms.

15. A composition as claimed in claim 14 wherein X is H, or the protonated residue of diethanolamine, triethanolamine or morpholine, $R^8$ is H, and $R^7$ and $R^{10}$ are each an amyl group.

16. A composition as claimed in claim 1 wherein the base composition is a metal working fluid and the inhibitor has the formula:

$$\begin{array}{c} CR^{11}CH_2CH_2COOX \\ \diagup \qquad \diagdown \\ (CH_2)_n \qquad C=O \\ \diagdown \qquad \diagup \\ CR^{12}CH_2CH_2COOX \end{array} \quad \text{IV}$$

wherein X is as defined in claim 1, $R^{11}$ and $R^{12}$ are the same or different and each is H or $-CH_2CH_2COOX$ wherein X has its previous significance and n is an integer from 5 to 15.

17. A composition as claimed in claim 16 wherein X is H, or the protonated residue of diethanolamine, triethanolamine or morpholine, $R^{11}$ is H, $R^{12}$ is $CH_2CH_2COOX$ wherein X is as defined above and n is 9.

18. A composition as claimed in claim 17 wherein X is the protonated residue of triethanolamine.

19. A composition as claimed in claim 1 wherein the composition is an oil-based functional fluid and $R^1$, $R^2$ and $R^3$ are each H, $R^4$ is as defined in claim 1, $R^5$ is an alkyl group having from 8 to 16 carbon atoms and X is H or a protonated amine residue or X, when $R^4$ is $-CH_2CH_2COOH$, is an alkyl or hydroxyalkyl function.

20. A composition as claimed in claim 1 wherein the composition is an oil-based functional fluid and $R^1$ is H, either $R^2$ and $R^4$ are each H or one is H and the other is $-CH_2CH_2COOX$ wherein X is as defined in claim 1, $R^3$ and $R^5$ are each alkyl having from 5 to 16 carbon atoms and X is H or a protonated amine residue or X, when $R^2$ or $R^4$ is $-CH_2CH_2COOH$, is an alkyl or hydroxyalkyl function.

21. A composition as claimed in claim 20 wherein $R^3$ and $R^5$ are each alkyl having from 8 to 16 carbon atoms.

22. A composition as claimed in claim 1 wherein the composition is an oil-based functional fluid and $R^1$ is H, either $R^2$ and $R^4$ are each H or one is H and the other is $-CH_2CH_2COOX$, $R^3$ and $R^5$ together are the group $-(CH_2)_m-$, wherein m is an integer from 9 to 15 and X is H or a protonated amine residue or X, when $R^2$ or $R^4$ is $-CH_2CH_2COOH$, is an alkyl or hydroxyalkyl function.

* * * * *